United States Patent [19]

Ilsink

[11] Patent Number: Plant 5,836

[45] Date of Patent: Dec. 23, 1986

[54] ROSE PLANT INTERSINA

[75] Inventor: G. Peter Ilsink, Leersum, Netherlands

[73] Assignee: Jackson & Perkins Company, Medford, Oreg.

[21] Appl. No.: 710,591

[22] Filed: Mar. 11, 1985

[51] Int. Cl.[4] ..... A01H 5/00

[52] U.S. Cl. ..... Plt./18

[58] Field of Search ..... Plt./11, 18, 19

*Primary Examiner*—James R. Feyrer

*Attorney, Agent, or Firm*—Manford R. Haxton

[57] ABSTRACT

A hybrid tea rose variety having long stems with few thorns, pointed buds desirable for cutting, pink coloring suffused over white, little fragrance, short peduncles, petalage of approximately 35.

1 Drawing Figure

This present invention relates to a new and distinct variety of rose plant of the hybrid tea class which was originated by crossing an unnamed variety with the variety Red Success, U.S. Plant Pat. No. 4,037.

The primary objective of this breeding was to produce a new rose variety with stems long enough for cut flowers, shapely, well formed buds and open flowers, good keeping ability, and a color near pink. This objective was substantially achieved along with other desirable improvements as evidenced by the following unique combination of characteristics which are outstanding in the new variety and which distinguish it from its parents as well as from all other varieties of which I am aware:

1. Abundantly produced stems with lengths generally over 18 inches;
2. Pointed buds of pink suffused over white;
3. Approximately 35 petals;
4. Relatively few thorns on stems;
5. Relatively short peduncles supporting flower buds; and
6. Very little fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Red Success, U.S. Plant Pat. No. 4,037.

Classification:

*Botanical.*—Rosa hybrid.

*Commercial.*—Hybrid tea.

FLOWER

Observations made from specimens grown in a greenhouse at Irvine, Calif. in January.

Blooming habit: Continuous.

Bud:

*Size.*—1¼" to 1½" when petals start to unfurl.

*Form.*—Pointed, broad base.

*Color.*—When sepals first divide, Near Red group 50D on edges of petals blending to near white at center of petals; when half blown, upper side of petals Near Red group 50D blending to near white on outer petals; lower side of petals Near Red group 50D blending to near white on outer petals.

*Sepals.*—Color: Green 138B. Three appendaged sepals very lightly appendaged, edges bearing numerous glands. Two appendaged sepals hairy edged.

*Receptacle.*—Color: Green 138B. Shape: Funnel, Size: Large. Surface: Smooth.

*Peduncle.*—Length: Short. Surface: Glandular. Color: Light green. Strength: Stiff, erect.

*Opening.*—Spiral-like opening.

Open bloom:

*Size.*—Large. Average open size 4".

*Borne.*—Singly.

*Stems.*—Long, strong.

*Form.*—When first open, high center. Permanence: Retains its form to the end; outer petal edges slightly curled.

*Petalage.*—Number of petals under normal conditions: Approximately 35.

*Color.*—Center of flower: Upper side of petals, Near Red Group 56C; reverse side of petals, Near Red group 56C. Base of petals, large area Near White. Major color: Pink (Red Group 56C).

*Variegations.*—None.

*Discoloration.*—General tonality at end of third day: Outer petals lighten to near white overlaid with Pink.

*Fragrance.*—Very slight.

Petals:

*Texture.*—Thick.

*Shape.*—Round.

*Form.*—Edges slightly quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Medium. Color: Yellow. Arrangement: Regular around styles.

*Filaments.*—Color: Yellow.

*Pollen.*—Lemon yellow.

*Styles.*—Color: Basal end white, distal end red.

*Stigmas.*—Color: Yellow.

PLANT

Form: Bush.

Growth: Vigorous, upright.

Foliage: Number of leaflets on normal mid-stem leaves: 7.

*Size.*—Medium.

*Quantity.*—Normal.

*Color.*—New foliage: Greyed Purple 184A overlayed on green. Old foliage: Green 139A.

Leaflets:

*Shape.*—Oval pointed.

*Texture.*—Leathery.

*Edge.*—Serrated.

*Serration.*—Single; small.

*Petiole.*—Rachis: Color: Green. Underside: With few prickles.

*Stipules.*—Long, bearded.

*Disease resistance.*—Normally resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.—On main canes from base: Few. On laterals from main canes: Few.*

*Form.*—Long base, hooked downward.

*Color when young.*—Light brown.

Small prickles:

*Quantity.*—On main stalks, few. On laterals, few.

*Color.*—Brown.

I claim:

1. A new and distinct variety of rose plant of the hybrid tea class, substantially as herein shown and described, characterized particularly as to novelty by the unique combination of its long stems having few thorns, pointed buds desirable for cutting, pink coloring suffused over white, little fragrance, short peduncles, petalage of approximately 35.

* * * * *

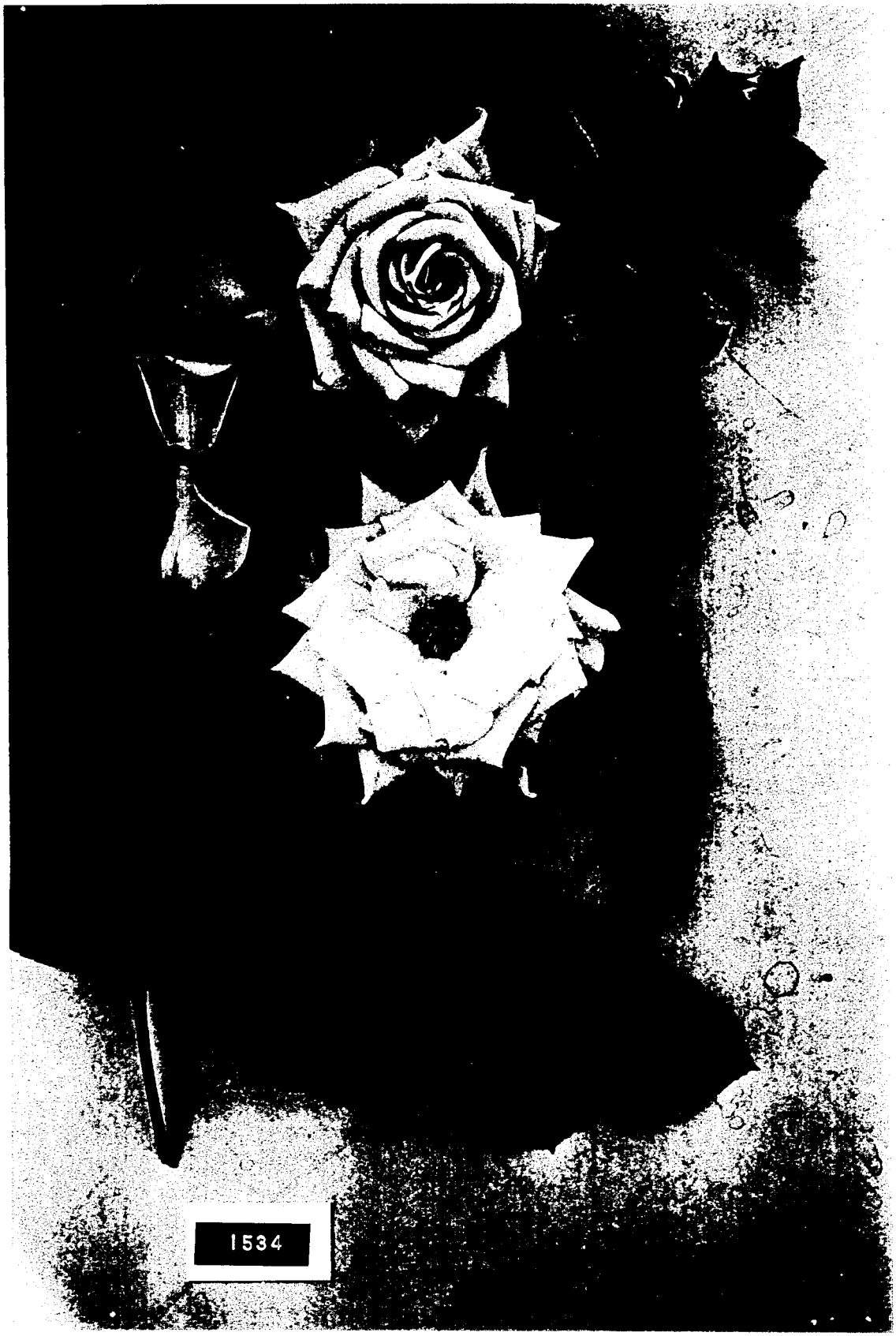
1534